United States Patent
Li et al.

(10) Patent No.: US 8,257,756 B2
(45) Date of Patent: Sep. 4, 2012

(54) BLACK SOYBEAN HULL EXTRACT, METHOD FOR OBTAINING, AND USE THEREOF

(75) Inventors: Yanmei Li, Beijing (CN); Fengying Zhou, Beijing (CN); Xiarui Dou, Beijing (CN)

(73) Assignee: Beijing Gingko-Group Biological Technology Co., Ltd., Beijing (CN)

( * ) Notice: Subject to any disclaimer, the term of this patent is extended or adjusted under 35 U.S.C. 154(b) by 300 days.

(21) Appl. No.: 11/830,442

(22) Filed: Jul. 30, 2007

(65) Prior Publication Data
US 2008/0145482 A1 Jun. 19, 2008

Related U.S. Application Data

(63) Continuation-in-part of application No. PCT/CN2006/003397, filed on Dec. 13, 2006.

(51) Int. Cl.
*A61K 36/00* (2006.01)
(52) U.S. Cl. .......................... 424/757; 424/725
(58) Field of Classification Search .................. None
See application file for complete search history.

(56) References Cited

FOREIGN PATENT DOCUMENTS

| CN | 1018838 B | 3/1989 |
|---|---|---|
| CN | 1040042 A | 2/1990 |
| CN | 1063031 C | 3/2001 |
| CN | 1483349 A | 3/2004 |
| CN | 1185351 C | 1/2005 |
| CN | 1733784 A | 2/2006 |
| CN | 200510036419.3 | 2/2006 |
| CN | 1844129 A | 10/2006 |
| JP | 2004-238303 | 8/2004 |
| WO | WO 2010/002972 | 1/2010 |

OTHER PUBLICATIONS

Takahashi et al. Antioxidant Activities of Black and Yellow Soybeans Against Low Sensity Lipoprotein Oxidation; J. Agric. Food chem. (2005) 53 pp. 4578-4582.*
Takahata et al. Highly Polymerized Procyanidins in Brown Soybean Seed Coat With a High Radical-Scavenging Activity; J. Acric. Food Chem. (2001), 49, pp. 5843-5847.*
Liu et al., "The Research of Cellulase and its Application," *Food and Fat*, 2004, 1:15-18 (English language abstract included).
Qi et al., "Production and Application of Cellulase," *Hebei Chemical Industry*, 2000, 1:25-26 (English language abstract included).

* cited by examiner

*Primary Examiner* — Patricia Leith
(74) *Attorney, Agent, or Firm* — Fish & Richardson P.C.

(57) ABSTRACT

Methods for preparing black soybean hull extracts and uses thereof. The methods can comprise: (1) extracting crushed black soybean hull with aqueous solution containing enzyme and filtering the extracted liquid; (2) ultrafiltration of the extract liquid with an ultrafiltration membrane; (3) absorbing the ultrafiltration liquid with an absorption resin or an ion exchange resin, and elution with ethanol to obtain purified extract liquid; (4) concentrating the purified extract liquid under vacuum; (5) spray drying the concentrated liquid. The extract can contain: 10-45% of cyanidin, 10-25% of catechin, and 40-80% of OPC, and with a total polyphenol content as high as 70-100%. The extract can be used for preparing drugs or food containing antioxidants, or used for improving metabolic syndrome or eyesight.

5 Claims, 3 Drawing Sheets

BLACK SOYBEAN HULL EXTRACT, METHOD FOR OBTAINING, AND USE THEREOF

CROSS-REFERENCE TO RELATED APPLICATIONS

This application is a continuation-in-part and claims benefit under 35 U.S.C. §120 of International Application No. PCT/CN2006/003397, having an International Filing Date of Dec. 13, 2006.

TECHNICAL FIELD

This document relates to an extracting method and an extract of a natural product, and in particular, to a method for extracting polyphenol from black soybean, to black soybean hull extracts obtained by the method, and to the use of the black soybean hull extracts.

BACKGROUND

Black soybean is also referred to as black bean, lu bean, liao bean, or lingwu bean. According to the theory of traditional Chinese medicine, black material can have an effect on kidney, and black soybean, being sweet-warm and innocuous, can affect kidney and spleen as well as heart meridian. Black soybean is thought to have function in tonifying kidney and improving physique, dehumidification and diuresis, as well as resisting aging and prolonging life. Eating black soybean is believed to improve skin, benefits look, replenish marrow, enhance strength, and increase appetite. Researchers have found that black soybean is highly nutritious, and is one of the five kinds of black food which are very popular in the market.

Researchers have shown that there are plentiful nutritious substances in the black soybean hull, and that black soybean has high protein content and low caloric content. Black soybean contains eighteen amino acids, especially the eight amino acids that are necessary for the human body. Black soybean also contains nineteen oleic acids, and the unsaturated fatty acid content of the black soybean is as high as 80%, with an absorptivity of over 95%. Black soybean can lower cholesterol content in blood besides meeting people's demand for fat. Generally, black soybean contains no cholesterol, but rather contains plant sterols, which cannot be absorbed by the human body. Plant sterols restrict the absorption of cholesterol by the body, as well as lower the content of cholesterol in blood. The levels of microelements in black soybean such as zinc, copper, magnesium, molybdenum, selenium, and fluorine also are very high. These microelements play an important role in resisting aging of the human body, lowering blood viscosity, etc. The black soybean hull is black in color and contains anthocyanidin, which is a good source of antioxidants and can eliminate free radicals from the body. Anthocyanidin is thought to have an especially good antioxidation effect in the acid environment of stomach.

Many human diseases are thought to be related to unbalanced free radicals, including cancer, diabetes, and ophthalmologic diseases. In normal situations, the generation and elimination of oxygen-derived free radicals is balanced. When too many oxygen-derived free radicals are generated or the antioxidant system is disabled, however, metabolism of oxygen-derived free radicals in the body will become unbalanced. Polyphenolic compounds are antioxidants, and can be divided into two categories: (1) monomers of polyphenol, including various flavonoids and chlorogenic acid, and composite polyphenolic compounds containing glycoside; and (2) oligomers or polymers polymerized from monomers, generally referred to as tannin. Anthocyanidin is one example of a polyphenol. See, Zheng et al., "Production and Use of Antioxidants," published by Chemical Industrial Publishing company.

Chinese Patent Application No. 200510036419.3 discloses a method for preparing black soybean seed hull anthocyanin comprising the following steps: 1) peeling black soybean seed hull as the raw material; 2) grinding black soybean seed hull into fine powder with a super-micro pulverizer, and processing the fine powder with a micro-wave machine; 3) extracting the crushed black soybean seed hull anthocyanin with 60-80% ethanol as the solvent; 4) condensing the extracted solution of the black soybean seed hull anthocyanin obtained in step 3 in a vacuum until the concentration of solid substances in the solution is over 40%; 5) degreasing, absorbing, and desorbing the extracted condensed solution obtained in step 4 with 65-75% ethanol, thus obtaining the purified extraction solution of the black soybean seed hull anthocyanin; and 6) condensing the extraction solution obtained in step 5 in a vacuum again until the concentration of solid substances is over 60%, and then freeze-drying the resulting substance to obtain the black soybean seed hull anthocyanin. The yield is said to increase remarkably when the fineness of the black soybean seed hull is over 320 meshes.

Chinese Patent Application No. 88104657.4 discloses methods for extracting a natural brown pigment, including an extracting method using water and an extracting method using ethanol. The extracting method using water is as follows: the seed hull of black soybean or brown soybean is added with 5-15 times of water, and is soaked for 10-24 hours, then is refluxed for 1 hour or boiled for 1-2 hours and then filtered. The aforesaid steps are repeated three times, and the filtrates are combined, decompressed and condensed, then 95% of ethanol is added into the condensed solution, and deposits are filtered after the condensed solution is placed still for a time. The resulting solution is then decompressed, concentrated, and dried to obtain the natural brown pigment. In the extracting method using ethanol, 15%-50% ethanol is used to soak the seed hull, and the other steps are the same as those in the extracting method using water.

Japanese Patent Application No. 2004-238303 discloses a method for extracting a black soybean seed hull extract composition. The method includes the following steps: the black soybean seed hull is extracted in an acid solution with a pH 1-2, then is neutralized until the pH reaches 3.0-4.0, and filtered, then desalted, condensed, and refined. The contents of substances are adjusted through an adding procedure, and then the resulting substance is dried to be the final product. According to the method, the content of the anthocyanin as the effective component is over 10% by weight, and the content of the polyphenol is over 50% by weight determined by UV absorbance analysis.

Although the extracted target substances are not the same for the above extracting methods, the methods have the same general defects. The yield obtained by the extracting method using ethanol is relatively high, but the production cost is also high; the extracting method using water is of low cost, but the yield is also low. Further, the purity of products obtained by extracting methods using water or ethanol is not high. Therefore, an extracting method by which higher yield and products of higher purity can be achieved is desired.

SUMMARY

The present document provides methods for preparing a black soybean hull extract (BSHE) that are cost effective and give an increased yield as compared to other methods known in the art. The methods provided herein can comprise:

(1) an extracting step: extracting the crushed black soybean hull with water solvent containing enzyme and filtering the extracted solution to obtain the filtration solution;

(2) an ultrafiltration membrane filtering step: filtering the filtration solution with an ultrafiltration membrane, thereby obtaining an ultrafiltration filtrate;

(3) a resin separating step: absorbing the ultrafiltration filtrate with absorbing resin or ion exchange resin, and eluting the same with ethanol, thereby obtaining purified extract solution;

(4) an concentrating step: condensing the purified extract solution in vacuum, thereby obtaining a condensed solution; and (5) a spray-drying step: spray-drying the obtained condensed solution, thereby obtaining BSHE.

According to the preparation method, the water solvent containing enzyme can contain cellulase or pectinase with a concentration of 0.05%-0.2%.

The preparation method further can comprise a step wherein the crushed black soybean hull is sieved with a screen of 60-80 meshes, wherein in the extracting step, the extracting temperature is 20-60° C., the extracting time is 1-2 hours, and the extracting steps are repeated 2-3 times.

According to the preparation method, in the ultrafiltration membrane filtering step, remaining enzyme and sugar of high molecular weight, as well as other dregs, can be removed, the diameter of the holes of the ultrafiltration membrane can be 0.1-10 um; the molecular weight cut-off can be 8000-10000 Da; the temperature can be 10-45° C.; the pressure can be controlled at 2-3 bar; and the flux can be 100-150 L/h.

According to the preparation method, 40-95% ethanol can be used for elution in the resin separating step. The resin can be an absorption resin of various polarities or an ion exchange resin of various intensities.

According to the preparation method, the content of the solid substance in the concentrated liquid obtained in the concentrating step can be up to 10%-30%, and the temperature of vacuum concentration can be below 60° C.

The present document further provides the BSHE prepared according to the methods disclosed herein, wherein the BSHE contains: 10-45% cyanidin, 10-25% catechin, and 40-80% oligomer proanthocyanidin (OPC), and wherein the total content of polyphenol is at least 60% (e.g., at least 70%, at least 80%, or at least 90%).

The present document further provides the use of BSHE prepared according to the methods disclosed herein, for preparing antioxidants and pharmaceuticals or foods that can ameliorate metabolic syndrome.

The present document further provides the use of BSHE prepared according to the methods disclosed herein, for improving eyesight.

The present document also provides a composition (e.g., a nutritious food composition) comprising BSHE, wherein the BSHE contains: 10-45% cyanidin, 10-25% catechin, and 40-80% of OPC, and wherein the total content of polyphenol is at least 60% (e.g., at least 70%, at least 80%, or at least 90%). The composition can be a dietary or food supplement.

This document also features a method for improving eyesight in a subject in need thereof, the method comprising administering to the subject an effective amount of the BSHE as described herein.

In addition, this document features a method for treating metabolic syndrome, the method comprising administering to a subject diagnosed with metabolic syndrome an effective amount of the BSHE as described herein.

In another aspect, this document features a method for preparing BSHE, comprising extracting crushed black soybean hull with an aqueous solution containing an enzyme. The method further can comprise filtering the extracted liquid to obtain a filtration liquid. The method also can further comprise filtering the filtration liquid with an ultrafiltration membrane to obtain an ultrafiltration liquid, absorbing the ultrafiltration liquid with a resin and then eluting with ethanol to obtain a purified extract liquid, concentrating the purified extract liquid under vacuum to obtain a concentrated liquid, and spray drying the concentrated liquid to obtain a BSHE. The ultrafiltration can include removing remaining enzyme, large molecule weight sugars, and other dregs; the aperture of the ultrafiltration membrane can be 0.1 μm to 10 μm, the molecular weight cut-off can be 8000 Da to 10000 Da; the temperature can be 10° C. to 45° C., the pressure can be controlled at 2 bar to 3 bar, and the flow rate can be 100 L/h to 150 L/h. The resin can be an absorption resin or an ion exchange resin. 40% to 95% ethanol can be used for said eluting. The content of solid substance in the concentrated liquid produced in the concentrating step can be 10% to 30%, and the temperature of the vacuum concentration can be below 60° C. The aqueous solution containing enzyme can contain cellulase or pectinase (e.g., 0.05% to 0.2% cellulase or pectinase). The method can further comprise sieving the crushed black soybean hull with a screen of 60-80 meshes, wherein the temperature for the extracting step is 20° C. to 60° C., and the extracting is performed for 1 to 2 hours and is repeated 2 to 3 times.

The advantages of the methods, extracts, and composition provided herein are as follows:

1. The fineness of the seed hull is 60-80 meshes, and needs not be too fine.

2. Compared with the cost of traditional alcohol solvents, the cost of the water solvent added with enzyme is reduced; while subsequent processing of the extraction solution obtained through extraction using water as the solvent can be conducted without condensation, and is easy to do; and compared with the acid water extraction process, the emission of effluent is decreased, which is helpful for environmental protection.

3. The content of polyphenolic substances is higher than that obtained through extracting methods using alcohol or water—as high as 80% or even 90% or more.

4. The yield using the preparation methods provided herein is higher than that of extracting methods using water and alcohol.

5. Various effective components can be extracted fully, and all the effective components can be retained to a great extent.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Unless otherwise described, the ratio and content referred to in the present document is by mass.

The term "black soybean hull extract" (BSHE) in the present document refers to compositions extracted from black soybean hull, wherein the total content of polyphenol is as high as 90% or more, cyanidin content is 10-45%, catechin is 10-25%, and OPC is 40-80%. The composition mainly comprises polyphenolic substance and has functions of antioxidant activity, improving eyesight, antimetabolic syndrome, etc.

The term "catechin" in the present document refers to catechin polyphenols, mainly comprising catechin and epicatechin. The term "the total content of polyphenol" refers to the total content of various polyphenolic substances (which mainly includes cyanidin, catechin, and OPC), and the value of the total content of polyphenol(s) is more than or equivalent to the total content of cyanidin, catechin, and OPC.

The BSHE extracting methods provided herein are mainly characterized in that the crushed black soybean hull is extracted with an aqueous solution containing enzyme as the solvent, and further, in that separation steps of ultrafiltration membrane filtration and resin absorption are employed. The method can comprise one or more of the following steps:

1. Peeling and Crushing Step: The seed hull of black soybean can be peeled (an existing peeler can be used), and the peeled black soybean seed hull can be crushed and sieved. A screen of 50-100 meshes can be used for the sieving, e.g., a screen of 60-80 meshes. The number of meshes of the screen can affect the quality of the extracts. If too fine of a screen is used (e.g., if the number of meshes is over 100, such as 200 or 300 meshes), there may be many impurities in the extract, and if a too rough of a screen is used (e.g., if the number of the meshes is below 50), the yield may be low and it may be hard to get the desired effective components. When a screen of 60-80 meshes is used, the desired results can be achieved. It will be understood that the peeling step for the black soybean and the grinding step for the hull can be separated from the extracting step, and can serve as the preparation step for the methods provided herein.

2. Extracting Step: Extraction can be conducted with an aqueous solution containing 0.05-0.2% enzyme as a solvent. The ground (or crushed) black soybean hull can be mixed with the solvent in a proportion of 1:10-15 by weight. The mixture can be heated and the temperature kept at 20-60° C. The extracting time can be 1-2 hours, and the extracting can be repeated two or more times (e.g., 2 times, 3 times, 4 times, or more than 4 times). The mixture can be filtered after each extracting, and filtrates can be combined. Filtration can be conducted by traditional filtering methods. Compared with extracting methods using water or ethanol, the yield can be improved or the cost can be reduced by extracting the crushed black soybean hull with a solvent of water containing enzyme. Compared with extracting methods using acid solution of pH 1-2, such as that disclosed by Japanese patent application 2004-238303, the methods provided herein have low equipment requirements (e.g., no anti-acid processing is required), and are environmentally friendly.

In the method provided herein, the selection of enzyme is very important. If the type or dosage of the selected enzyme is improper, the effective components of the product will be ruined. The inventors have found that better results are achieved using pectinase or cellulase.

Pectinase (or pectase) mainly comprises pectin lyase, polygalacturonase, pectate lyase, and pectinesterase. Pectinase can effectively decompose the pectin in plant tissue. Pectic substance is highly esterified polygalacturonic acid. When pectinase acts on a pectic substance, pectin lyase, polygalacturonase, and pectate lyase act directly on the glycosidic linkage inside the molecular chain of the pectic polymer, and the pectinesterase hydrolyzes polygalacturonate to create more positions for polygalacturonase and pectate lyase. Pectinase can be extracted from plants such as tomato, or from microorganism culture. Pectinase also is commercially available.

Any suitable concentration of pectinase can be used. A concentration from about 0.05% to about 0.2% (e.g., about 0.075%, about 0.1%, about 0.125% about 0.15%, or about 0.175%) can be particularly useful. If the concentration of pectinase in the aqueous solution is below 0.05%, the yield can be low, and it can be hard to extract fully effective components. If the concentration of pectinase in the aqueous solution is above 0.2%, a portion of the desired components may be ruined and the cost will be increased.

Cellulase also can be used. The inventors have observed that cellulase can be more effective than pectinase, as it can reduce the viscosity of the extract, thus facilitating filtration. "Cellulase" refers to the generic term of a group of enzymes that can hydrolyze the $\beta$-1,4-glycoside bonds of cellulose to convert cellulose into cellobiose and glucose. Cellulase is not a single enzyme, but rather is a multi-component system of enzymes that have synergetic effects. See, He et al., "Cellulase and its Current Situation of Application," *Food and Fat,* 2004, 1:15-18. Sources for cellulose, include, for example, insects and microbes, such as bacteria, antinomycetes, fungi, etc. Microbial fermentation can be an effective way to produce cellulase on a large scale. Production processes for cellulose include solid fermentation and liquid fermentation. Raw materials for production include, for example, bran, straw powder, waste paper, corn powder, and inorganic salts. See, Qi et al., "Production and Application of Cellulase," *Hebel Chemical Industry,* 2000, 1:25-26. Cellulase is mainly used in the food industry, forage industry, aquatic product industry, detergent industry, and textile industry. The extraction methods provided herein can include the use of commercially available cellulase. The concentration of cellulase in the aqueous solution can be about 0.05 to about 0.2% (e.g., about 0.075%, about 0.1%, about 0.125% about 0.15%, or about 0.175%), which is similar to the amount of pectinase used. Without being bound by a particular mechanism, the mechanics of applying cellulase are as follows: cellulase may promote decomposition of cellulose and hemicellulose and dissolution of the plant cellular wall to dissolve more contents of plant cells. Furthermore, cellulase can degrade large molecular amylase, which is not easily digested into small molecular materials.

3. Ultrafiltration Membrane Filtering Step: The filtrate can be filtered with an ultrafiltration membrane, thereby obtaining an ultrafiltration filtrate. Remaining enzymes, large molecular sugars and other dregs can be removed during the filtering step. The aperture of the ultrafiltration membrane can be from about 0.1 to about 10 µm, the molecular weight cut-off (MWCO) can be from about 8000 to about 10000 µm, the temperature can be about 10° C. to about 45° C., the pressure can be controlled at about 2 to about 3 bar, and the flow rate can be about 100 to about 150 L/h. Ultrafiltration membranes can be commercially obtained. It is noted that ultrafiltration membrane filtration is not required in the present methods, however, as the separation method of alcohol deposition also can be used.

4. Resin Separatin Step: This step can include adsorbing the ultrafiltration filtrate with an adsorption resin or an ion exchange resin, and eluting the same with ethanol (e.g., about 40% to about 95% ethanol), thereby obtaining a purified extract solution. Various polarities of adsorbing resin or various strengths of ion exchange resin can be used, although current adsorbing resins of medium polarity or cation ion exchange resins can be particularly useful.

5. Concentrating Step: The purified extract solution can be concentrated to obtain a condensed solution. By condensation under reduced pressure, the solution can be concentrated until the concentration of solid substances in the condensed solution is about 10% to about 30%. The condensing temperature can be below 60° C. (e.g., about 50° C. to about 55° C.), and the vacuum degree can be about −0.08 MPa. When the temperature is lower than 40° C., the condensing rate may be too slow, and when the temperature is higher than 60° C., too much product may be lost.

6. Drying Step: The obtained condensed solution can be spray dried to obtain the BSHE. Spray drying can be carried out using standard spray drying equipment. If the method includes ultrafiltration membrane filtering, resin separating, and spray drying, very little product loss may be achieved. This may help to further increase the yield of BSHE.

BSHE obtained by the methods provided herein typically is highly purified. The total content of polyphenol in the BSHE may reach 60% or higher (e.g., at least 70%, at least 80%, or at least 90%), wherein the content of cyanidin reaches about 10% to 45%, the content of catechin reaches about 10% to 25%, and the content of OPC reaches about 40% to 80%.

It is appreciated that traditional separating methods, for example, methods including condensing, alcohol depositing, and drying steps, may be applied after extracting the crushed black soybean hull using an aqueous solution containing an enzyme. However, by use of the methods provided herein, the yield and the purity may be increased. Further the methods provided herein are simple, and the production of BSHE is feasible at low cost. In addition, the products contain various kinds of nutrients, and also can be used in health care compositions.

BSHE obtained by the methods provided herein is rich in polyphenols, and may be used alone or in combination with other effective materials to produce a nutritional food composition. Such compositions can be used to prevent or treat (e.g., to improve symptoms) physiological dysfunction that is related to high oxidation activity and low demolition of free radicals, including, for example, metabolic syndrome, eyesight reduction or impairment, and eyestrain. The nutritional composition can be a food supplement (e.g., a capsule or pastille, or a filled in micro-sized capsule), or can be included in a food (e.g., in alcohol-free soft drinks, milk, juice, pastries, or in teabags). BSHE also can be prepared into a vegetable pharmaceutical composition. Such a vegetable pharmaceutical composition can be in a form suitable for oral administration, for example, a pastille, hard or soft capsule, aqueous solution or syrup, or a form that is suitable for external use. The dosage of BSHE can be adjusted on demand.

Partially or highly purified polyphenol in an effective dose can be formulated into a pharmaceutical composition with a pharmaceutically acceptable carrier, which can be used to treat physiological dysfunction caused by oxygen free radicals. An "effective dose" refers to a dose of polyphenol sufficient to show a beneficial effect. The effective dose can be varied, as a person skilled in the art can understand, depending on the method of administration, the excipient used, and whether other optional co-employed therapeutics are used.

The toxicological research of BSHE and the application of the extract in the aspects of curing eyestrain, eyesight dropping, and metabolic syndrome also are included in the scope of the present document. Experiments in vitro or in vivo can be used to evaluate the anti-oxidation effects of the nutritional or pharmaceutical compositions provided herein. For example, the ability of compositions containing BSHE to reduce or prevent formation of free radicals can be evaluated via in vitro or in vivo experiments.

Using an ortho-phenanthroline $Fe^{2+}$ oxidation method to test hydroxyl free radical levels, the inventors observed that BSHE has the effect of scavenging hydroxyl free radicals, and that its scavenging capability is related to the concentration of pharmaceuticals. The scavenging rate is positively correlated with the concentration, and its $IC_{50}$ is quite a bit lower than the $IC_{50}$ of ascorbic acid (Vc) under the same experimental conditions. The inventors concluded that BSHE has greater scavenging capabilities than ascorbic acid, and has significant anti-oxidation effect in vitro.

BSHE has shown no toxic effects in a series of toxic experiments, such as orally acute toxic tests in mice, Ames tests, mouse bone marrow cell micro-nuclei tests, mouse sperm malformation tests, etc. Thus, BSHE can be considered as safe and innocuous to the human body.

The effect of BSHE obtained by the methods disclosed herein on the human body with respect to eyesight protection and metabolic syndrome was investigated. As described in greater detail below, sixty young people whose far eyesight was degraded and whose age ranged from 7 years to 28 years were randomly divided into a test group and a control group. Those in the test group took BSHE orally at 300 mg/day, and each person in the control group took the same dose of placebo every day. After two months, changes in eye symptoms and eyesight were assessed. Compared to the control group, the BSHE test group showed significant improvement in eye symptoms and distance eyesight. It was concluded that BSHE is capable of reducing eyestrain symptoms and improving distance eyesight of early near-sighted people and lightly near-sighted people.

Sixty-two patients diagnosed with metabolic syndrome whose ages ranged from 32 years to 81 years were randomly divided into a test group and a control group. Besides their daily regular treatment, those in the test group further took BSHE orally at 300 mg per day. Those in the control group took the same dose of placebo. After two months, changes in weight, blood lipid, blood pressure, and blood sugar on an empty stomach and two hours after a meal were measured. It was observed that weight, blood pressure, blood lipid, and blood sugar were significantly decreased in the test group. It thus can be concluded that adding BSHE to regular treatment may help drugs to treat or cure metabolic syndrome, and may be advantageous to prevent the occurrence and aggravation of diabetes and cardiovascular diseases caused by metabolic syndrome.

The invention will be further described in the following examples, which do not limit the scope of the invention described in the claims.

EXAMPLES

Example 1

BSHE Preparation 1

One thousand g crushed black soybean hull (passing through a sieve with 60 meshes) as the raw material was extracted with 15 L of an aqueous solvent solution containing 0.08% pectase at 40° C. for two hours, then filtered. The extraction process was conducted twice and during the second extraction process, 10 L aqueous solution with the same pectase concentration was added. The extraction liquid from the two processes was combined (27 L) and then filtered through an ultrafiltration membrane until the resulting effluent was about 20 to 25 L. The effluent was subsequently resin separated and purified (at a flow rate of 20 to 40 L/h), and then eluted with 40-95% ethanol. The ethanol-eluting liquid was combined and then concentrated until the solid substance in the concentrated solution was equal to or more than 30%. Thirty-five g BSHE was obtained, and the yield was 3.5%.

Figure 1:
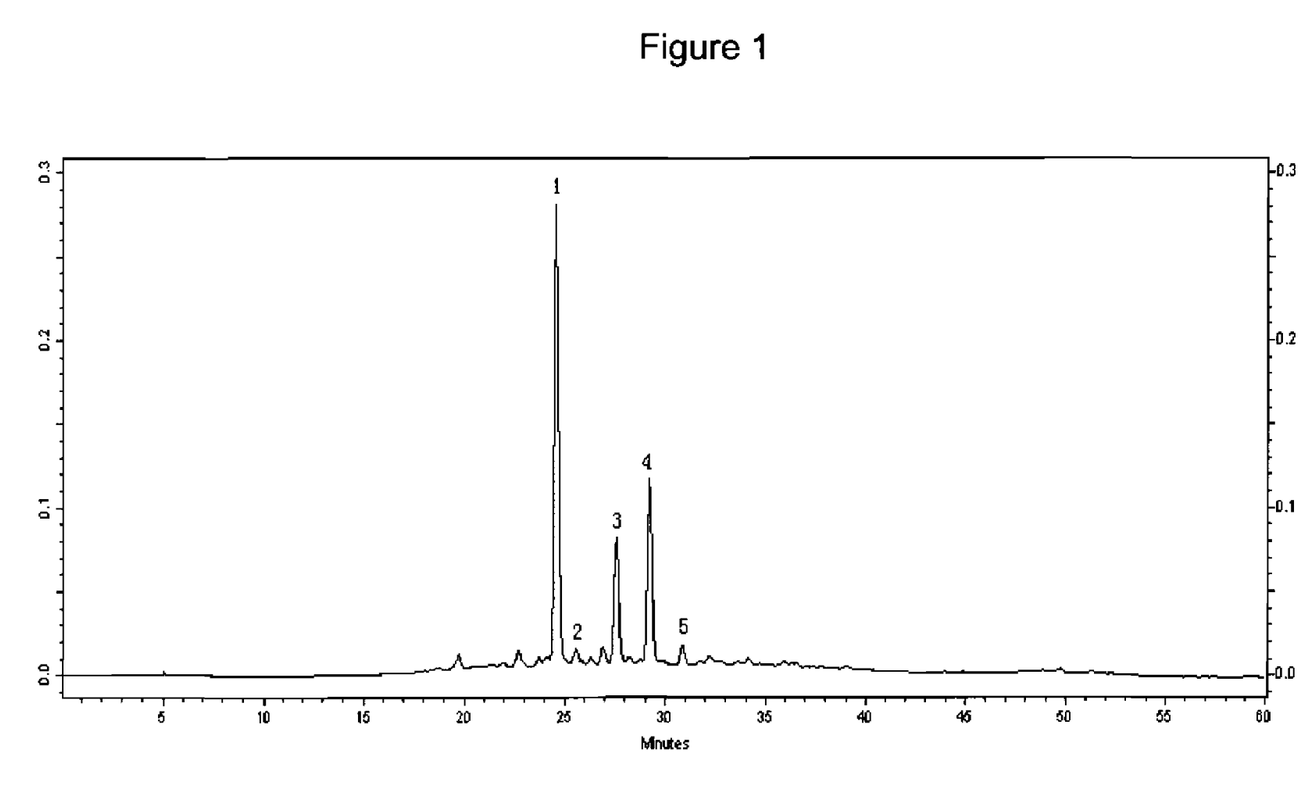
FIG. 1 is a chromatogram of BSHE produced as described in Example 1.

The resulting BSHE product contained 32.54% cyanidin, 15.63% catechin, and 50.01% OPC, and the total content of polyphenol was up to 98.18% or more. The components were measured using a high efficiency liquid phase chromatogram (HPLC), and the chromatogram is shown in FIG. 1. In the chromatogram, absorbing peak 1 corresponds to cyanidin, absorbing peak 2 corresponds to catechin, absorbing peak 4 corresponds to epicatechin, absorbing peak 3 corresponds to the dimer of OPC, and absorbing peak 5 corresponds to the trimer of OPC.

The condition of the measurement of chromatogram were:
1. the chromatogram column: ODS C18, 5 μm, 250 mm×4.6 mm
2. flow phase A: 9% acetonitrile, 0.1% glacial acetic acid (aqueous solution) flow phase B: 40% acetonitrile (aqueous solution)

| time (min) | flow phase A | flow phase B |
|---|---|---|
| 0.01 | 94% | 6% |
| 10.00 | 94% | 6% |
| 50.00 | 0 | 100% |
| 55.00 | 0 | 100% |
| 60.00 | 94% | 6% |

3. flow rate: 0.8 ml/min
4. determination wave length: 280 nm
5. temperature of the column: 40° C.

Example 2

BSHE Preparation 2

One thousand g crushed black soybean hull (passing through a sieve with 90 meshes) as the raw material was extracted at 55° C. with 15 L of an aqueous solvent solution containing 0.2% cellulose. The temperature was maintained for two hours, and the extract was filtered. The extraction process was conducted twice, and during the second extraction process, 10 L of aqueous solution of the enzyme at the same concentration was added. The remaining steps were as described in Example 1. Forty-eight g of BSHE were obtained, and the yield was 4.8%. The resulting BSHE product contained: 12.52% cyanidin, 13.50% catechin, 54.01% OPC, and the total content of polyphenol was up to 80.03%.

Example 3

BSHE Preparation 3

The preparation steps of Example 3 were the same as those of Example 1, except that the aqueous solution contained 0.08% cellulase instead of 0.08% pectase. Thirty-eight g of BSHE were obtained, and the yield was 3.8%. The resulting BSHE product contained: 27.43% cyanidin, 11.25% catechin, and 54.12% OPC, and the total content of polyphenol was up to 92.80%.

Example 4

BSHE Preparation 4

One thousand g crushed Black Soybean Hull (passing through a sieve with 70 meshes) as the raw material was extracted at 50° C. with 15 L of an aqueous solvent solution containing 0.1% cellulose. The temperature was maintained for 1.5 hours, and the extract was filtered. The extraction process was conducted twice, and during the second extraction process, 10 L of the aqueous enzyme solution was added. The remaining steps were the same as those described in Example 1. Fifty-five g of BSHE was obtained, and the yield was 5.5%. The resulting BSHE product contained: 13.52% cyaniding, 11.70% catechin, and 52.01% OPC, and the total content of polyphenol was up to 77.23%.

Example 5

Comparative BSHE Preparation Using 50% Ethanol

One thousand g crushed black soybean hull (passing through a sieve with 60 meshes) as the raw material was extracted at 40° C. with 15 L of a 50% ethanol solution as a solvent. The temperature was maintained for 2 hours, and the extract was filtered. The extraction process was conducted twice, and during the second extraction process, 10 L of a 50% ethanol solution was added. The remaining steps were the same as those described in Example 1. Three g of BSHE were obtained, and the yield was 3%. The resulting BSHE product contained: 9.63% cyanidin, 7.53% catechin, and 30.82% OPC, and the total content of polyphenol was 47.98%.

Example 6

Comparative BSHE Preparation Using Water

One thousand g crushed black soybean hull (passing through a sieve with 60 meshes) as the raw material was extracted with 15 L water as a solvent, and circumfluence was conducted twice. The extraction process was conducted twice. The filtrates from the two processes were combined and concentrated. The remaining steps were the same as those described in Example 1. One and a half g of BSHE were obtained, and the yield was 1.5%. The resulting BSHE product contained: 5.61% cyanidin, 10.83% catechin, and 35.93% OPC, and the total content of polyphenol was 52.37%.

It can be seen that the yield using the aqueous solution containing the enzyme as the extraction agent was higher than the yields obtained using ethanol or water as the extraction agent. The total content of polyphenol using the aqueous enzyme solution also was higher than the polyphenol content obtained using the ethanol or water, even though the other conditions were the same.

Example 7

Evaluation of BSHE Toxicity

Based on the mice acute toxicity test, the maximum tolerable dosage of BSHE is more than 8 g/kg body weight. When the highest dosage of the sample was 100 times the recommended human dosage (300 mg/kg), the results did not indicate any mutagenicity based on the Ames test, mouse marrow cell microkernel test, and mouse semen abnormality test. Consequentially, it is believed that the extract of black soybean is safe for humans in terms of toxicology.

Example 8

Anti-Oxidation Effects of BSHE in Vitro

Materials and methods—test drug and reagent: Extract of black soybean hull A (containing cyanidin 12.52%, catechin 13.50%, and OPC 54.01%). Orthophenanthroline, hydrogen peroxide, ascorbic acid (VC), and $FeSO_4 \cdot 7H_2O$ were all analytical pure reagents made in China.

Materials and methods—instruments: An LSY constant temperature water bath was obtained from a Beijing medical instrument manufacturer, and a UV-2000 spectrophotometer was from Tainike, Shanghai Instrument Co., Ltd.).

Test method—reagent preparation: Reagents included 0.1% $H_2O_2$ (V/V), a 5 mmol/L anhydrous ethanol solution of orthophenanthroline, 0.75 mmol/L $FeSO_4$, a 0.2 mmol/L phosphoric acid buffer solution (PBS; pH=7.4), BSHE A, prepared with double distilled water and diluted to concentrations of 0.5, 0.25, 0.125, and 0.0625 mg/ml, and ascorbic acid, prepared at concentrations of 4, 2, 1, and 0.5 mg/ml with double distilled water.

Test method—measuring hydroxyl free radicals: The clearing of hydroxyl free radicals was tested using an orthophenanthrolin $Fe^{2+}$ oxidation method to further evaluate the anti-oxidation capacity of BSHE A.

(1) 2 ml PBS, the test drug at the concentrations listed above, and 1 ml ascorbic acid were sequentially added to a disposable 10 ml polyethylene test tube and shaken. 0.35 ml of 5 mmol/L orthophenanthroline solution and 1 ml 0.75 mmol/L $FeSO_4$ were added and mixed fully. 1 ml of 0.1% $H_2O_2$ was added, and the tube was vibrated for 1 minute. The tube was incubated at 37° C. for 60 minutes, and the absorbency value Aa of the reaction system at $\lambda=510$ mm was measured using a UV-2000 spectrophotometer.

(2) The 1 ml of test drug in (1) was replaced with 1 ml deionized water, while the other conditions were the same as in (1). The absorbency value Ab was measured.

(3) The 1 ml $H_2O_2$ in (2) was replaced with 1 ml deionized water, while the other conditions were the same as in (2). The absorbency value Ac was measured.

(4) The clearance rate (d) of .OH by the test drug and the positive comparison was calculated according to the following equation:

$$d = \left(1 - \frac{A_a - A_c}{A_b - A_c}\right) \times 100\%$$

The total volume of reaction was 5.35 ml. The final concentrations of ascorbic acid thus were 0.748 mg/ml, 0.374 mg/ml, 0.187 mg/ml, and 0.093 mg/ml, while the final concentrations of BSHE A were 0.093 mg/ml, 0.047 mg/ml, 0.023 mg/ml, and 0.012 mg/ml. Five samples were tested in each group. The clearance rate of .OH was calculated individually and then average values were calculated. The results are shown in Table 1.

TABLE 1

Clearance effects of ascorbic acid on hydroxyl free radical (n = 5)

| Final concentrations (mg/ml) | Clearance rate of •OH (d) |
| --- | --- |
| 0.748 | 91.29 ± 3.26 |
| 0.374 | 50.32 ± 4.29 |
| 0.187 | 4.21 ± 1.32 |
| 0.093 | 0.212 ± 2.47 |

Figure 2:
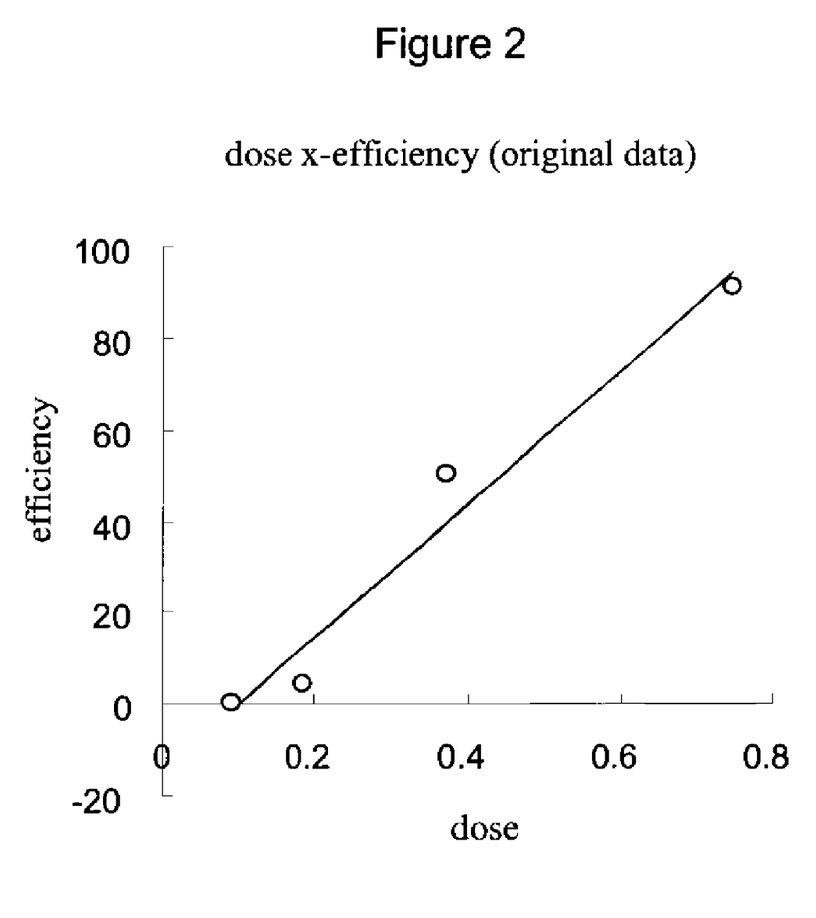
FIG. 2 is a fitted line showing the clearance function of ascorbic acid to hydroxy free radical.

In this test, when testing the clearance effect of BSHE on hydroxyl free radicals, ascorbic acid, the known clearance agent of .OH, was used as a positive comparison to verify the reliability of the method. Its fitted line was Y=−14.6996+146.1028X, and the regression coefficient was 0.983. The $IC_{50}$ was 0.4014 mg/ml, as shown in FIG. 2.

TABLE 2

Clearance effect of BSHE A on hydroxyl free radicals (n = 6)

| Final concentrations (mg/ml) | Clearance ratio of •OH (d) |
| --- | --- |
| 0.093 | 89.87 ± 11.07 |
| 0.047 | 39.52 ± 3.33 |
| 0.023 | 14.96 ± 1.79 |
| 0.012 | 3.39 ± 2.00 |

Figure 3:
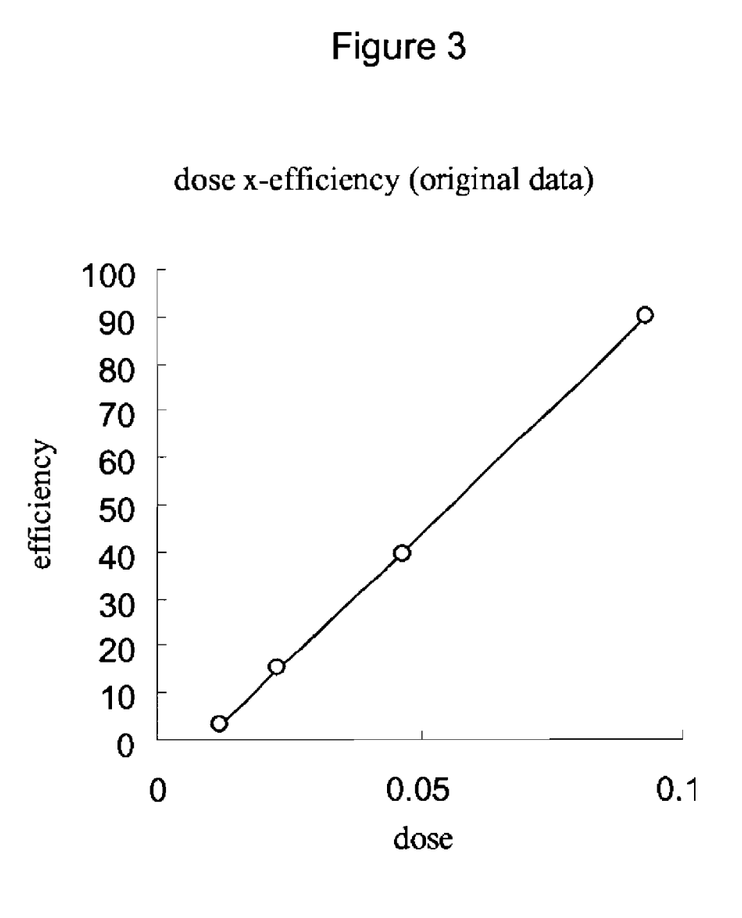
FIG. 3 is a fitted line showing the clearance function of BSHE to hydroxy free radical.

The fitted line was Y=−9.5012+1060.1879X, with a regression coefficient of 0.9999. The $IC_{50}$ was 0.0456 mg/ml, as shown in FIG. 3.

In the reaction system of this test, the aqueous solution of BSHE can combine with the hydroxyl free radicals produced from the Fenton reaction, reducing the oxidation of $Fe^{2+}$ due to the free hydroxyl radicals. The clearance effects of BSHE on free hydroxyl radicals was tested through measurement of the absorbency value of the reaction system. A portion of $Fe^{2+}$ is oxidized to $Fe^{3+}$ by hydroxyl free radicals, both of which coexist in the reaction system for a short time.

The drug may enhance the absorbency value of the reaction system by combining with hydroxyl free radicals to reduce the oxidation on $Fe^{2+}$, increasing the concentration of the combination (conjugation substance) of orthophenanthroline-$Fe^{2+}$ in the reaction system, and showing the clearance effect of the drug on .OH.

BSHE may combine with hydroxyl free radicals via the mechanism described above, reducing the oxidation of $Fe^{2+}$ due to hydroxyl free radicals, thereby showing the effect of eliminating hydroxyl free radicals. There was an obvious amount-effect relationship between the eliminating capacity of BSHE and the concentration of the drug, where the elimination ratio of BSHE was positively correlated with the concentration of the drug, and the $IC_{50}$ was 0.0456 mg/ml. On the other hand, under identical test conditions, the $IC_{50}$ of ascorbic acid (Vc) was 0.4014 mg/ml, which indicates that the clearance capacity of BSHE for hydroxyl free radicals is stronger than that of ascorbic acid, and that BSHE has significant antioxidation effects in vitro.

Example 9

In Vivo Effects of BSHE on Eyesight

Sixty volunteers with reduced distant vision, ranging from 7 to 28 years of age, were selected. The recruiting criteria for tested persons included: 4.0<=naked eye distance vision<5.0; naked eye near vision≧5.0; it was considered pseudomyopia or myopia if diopter was ≦3D after mydriatic test. Exclusion criterion of the tested persons included: persons of an age not from 7 to 28 years; persons with infective eye diseases and other eye diseases such as corneal nebula, keratoconus, or cataracts; persons with eyeground diseases or having cardiovascular diseases, brain vascular diseases, diabetes, or serious diseases of the liver, kidney, or hematogenic system; persons with psychopathy; persons who had been using other relevant drugs or therapeutics for an extended time and who were not currently pausing from their therapeutics; and persons who failed to eat according to regulation, failed to judge the function, or did not have complete and accurate judgment of function and safety.

Test design and requirements of grouping: Comparison within each group and between groups were used in this test. The tested persons were randomly divided into a test group and a control group with 30 individuals in each group, according to eyesight level.

Dosage and usage: In the test group, each person orally took three 100 mg doses of BSHE per day. In the control group, the placebo was administrated at the same dosage. The test duration was 8 weeks.

Observation parameters: Observations monitored included self-sensed symptoms of eyes (such as eye dryness, blurred vision, and tired eyes), as well as changes in distant vision. A determination of effectiveness was set at an improvement in distant vision of naked eyes≧2 showing the drug as effective.

Statistical method: A t test was used for statistical evaluation of eyesight changes, a paired t test was used for comparison information within the same group, and a grouped t test was used for comparison of averages between groups.

Results: 60 persons with nearsightedness were observed. The test group included 17 males and 13 females ranging from 8 to 28 years of age, with an average age of 14.32 years. The control group included 14 males and 16 females ranging from 7 to 28 years of age, with an average age of 14.40 years.

After taking BSHE, for the tested persons, the major uncomfortable symptoms of eyes were significantly improved. The improvement rate of eye dryness, blurred vision and eye tiredness were 60.00%, 56.00% and 62.96%, respectively, each of which was statistically different as compared with the control group (P<0.05).

After taking BSHE, there was an apparent improvement in vision within the test group, with a statistically significant difference from vision before testing (P<0.01). The total efficiency ratio was up to 63.33%, and as compared with the control group there was a statistically significant difference (P<0.01), as indicated in Table 3 and Table 4.

TABLE 3

Comparison of changes in distant vision of the naked eye before and after taking the drug ($\bar{x} \pm s$, n = 60)

| Group | Before administration | After administration | Difference |
| --- | --- | --- | --- |
| Test group | 4.55 ± 0.21 | 4.66 ± 0.25 | 0.60 ± 0.08** |
| Control group | 4.56 ± 0.23 | 4.61 ± 0.22 | 0.03 ± 0.03ΔΔ |

**comparison of the test group itself before and after administration; P < 0.01
ΔΔcomparison between groups before and after administration: P < 0.01

TABLE 4

Comparison of improvement ratio of distant vision for naked double-eyes between before administration and after administration ($\bar{x} \pm s$, n = 60)

| Group | Efficacy | Inefficacy | Total effect ratio |
| --- | --- | --- | --- |
| Test group | 38 | 22 | 63.33 |
| Control group | 2 | 58 | 3.33ΔΔ |

ΔΔcomparison in groups between groups before and after administration: P < 0.01

Thus, it was observed that youths with myopia obtained significant improvement in terms of both the naked eye distant vision and the uncomfortable symptoms of eyes after orally taking BSHE for 8 weeks. Vision tiredness involves a variety of symptoms that are mainly presented as the discomfort of eyes that is caused by longtime or excess eye usage without timely and effective relaxation. There are two possible inducements. One is that when eyeballs are in a searching and/or staring situation for a long period of time, the metabolism in extra ocular muscles and ciliary muscles is increased, causing increased accumulation of metabolism waste (including oxygen free radicals), such that muscle cell structure is damaged and functions are degraded. Another inducement is that visual cells are excessively depleted while the required nutriments are deficiently supplied, such that the recovery time for the macula and retina are extended. It has been observed that anthocyanin is capable of effectively improving the recovery time for macula of human eyes, especially for the identification of middle and high spatial numbers in a dark environment. Consequently, anthocyanidin is considered to be capable of increasing the blood current of microcirculation on the eyeground, speeding the substance metabolism exchange and enhancing the protection effect on the capillary vessel, thus has the effect of improving the recovery time of the macula and night vision. This could be related to the fact that anthocyanidin can promote the regeneration of the rhodopsin of retinal rod cells. In addition, anthocyanidin is an effective antioxidant that can clear the toxic oxygen free radical in vivo so as to protect histiocytes. Such pharmacological actions of anthocyanidin may be the basis of the vision protection capabilities of BSHE containing plenty of anthocyanidin.

Example 10

Anti-Metabolic Syndrome Effects of BSHE

Tested subjects: Based on the diagnosis criteria (see Table 5) proposed in 2001 by the Adult Treatment Group III (ATP III) of the U.S. National Cholesterin Treatment Education Program (NCEP), the subjects were selected from volunteers. Sixty-two cases were selected as satisfying the criteria, and were randomly divided into a treatment group and a control group. The treatment group included 18 males and 13 females, ranging from 33 to 81 years of age (the average age was 54.0 years), and the control group included 15 males and 16 females ranging from 32 to 79 years of age (the average age was 53.5 years).

TABLE 5

Diagnosis criteria metabolic syndrome

| Diagnosis criteria (require meeting any 3 of the following 5) | Reference critical points |
|---|---|
| Waistline | Male: 102 cm; Female: ≧88 cm |
| Triglyceride levels | ≧1.67 mmol/L or taking medication for reducing triglyceride |
| High density lipoprotein levels | Male: <1.04 mmol/L; Female: <1.29 mmol/L or taking medication for increasing high density lipid protein |
| Blood pressure | Systolic pressure ≧ 130 mmHg or diastolic pressure ≧ 85 mmHg, or taking medication for reducing blood pressure |
| Blood sugar under limosis | ≧6.1 mmol/L or taking medication for reducing blood sugar |

Test method: Subjects in the treatment group took oral BSHE 3 times/day at a dose of 100 mg/time, while patients in the control group were given a placebo at the same dosage. The test duration was 8 weeks.

Observation Parameters:

1) Body weight (kg) was measured in the early morning under conditions of limosis. Defecation and emiction also were measured before administration of drug or placebo and after administration for 8 weeks.

2) Blood lipid change (total cholesterin and triglyceride) were measured before and after the 8 week administration.

3) Changes in blood pressure were measured before taking and after the 8 week administration.

4) Blood sugar changes at limosis and 2 hours after a meal were measured before and after the 8 week administration.

Results: Body mass upon admission was 62.2±8.3 kg in the treatment group, and 61.8±7.8 kg in the control group, with no obvious difference therebetween (P>0.05). After administration of drug or placebo for 8 weeks, however, body mass in the treatment group was 58.4±7.5 kg, which was significantly decreased as compared with body mass before treatment (P<0.05). In contrast, body mass in the control group was 60.1±7.6 kg, with no significant difference from that before treatment (P>0.05).

Total cholesterin and triglyceride were significantly reduced after administration in both the treatment group and the control group (P<0.01; P<0.05, respectively). There was a significant difference (P<0.01) in reduced levels of total cholesterin between the treatment and control groups after administration, while there was no significant difference in levels of triglyceride between the two groups (P>0.05). See, Table 6.

TABLE 6

Changes in blood lipid of patients with metabolic syndrome before and after administration ($\bar{x} \pm s$, n = 31)

| | Total cholesterin (mmol/L) | | | Triglyceride(mmol/L) | | |
|---|---|---|---|---|---|---|
| | Before administration | After administration | P value | Before administration | After administration | P value |
| Treatment group | 7.0 ± 1.0 | 4.2 ± 0.9 ΔΔ | <0.01 | 2.5 ± 1.7 | 1.4 ± 1.0 | <0.05 |
| Control group | 6.8 ± 1.1 | 5.8 ± 0.9 | <0.01 | 2.5 ± 1.6 | 1.6 ± 0.9 | <0.05 |

ΔΔ comparison between groups before and after administration. P < 0.01

Before taking medicine, subjects having normal blood pressure within the treatment and control groups numbered 16 cases (51.6%) and 17 cases (54.8%), respectively, with no obvious difference therebetween. After administration, however, the number of subjects with normal blood pressure in the treatment and control groups were 22 cases (70.9%) and 19 cases (61.3%), respectively, which was significantly different as compared with each other (P<0.05).

Blood sugars measured under conditions of limosis and 2 hours after eating were significantly decreased in both the treatment and control groups. For the decreased amount of blood sugar measured 2 hours after dinner, there was a statistically significant difference between the treatment and control groups (P<0.01), while there was no significant difference between the two groups for the decreased amount of blood sugar under limosis (P>0.05). See Table 7.

TABLE 7

Changes in blood sugar of patients with metabolic syndrome before and after administration ($\bar{x} \pm s$, n = 31)

| | Blood sugar at limosis (mmol/L) | | | Blood sugar 2 hours after eating (mmol/L) | | |
|---|---|---|---|---|---|---|
| | Before administration | After administration | P value | Before administration | After administration | P value |
| Treatment group | 11.7 ± 2.3 | 7.3 ± 1.0 | <0.01 | 16.0 ± 2.9 | 11.1 ± 1.5 ΔΔ | <0.01 |
| Control group | 10.6 ± 1.5 | 7.9 ± 0.9 | <0.05 | 14.8 ± 1.6 | 12.9 ± 0.9 | <0.05 |

ΔΔ Comparison between groups before and after administration: P < 0.01

Based on the above, it has been observed that taking BSHE in addition to normal treatment can help with treatment of metabolic syndrome, contributing to reduction in levels of body weight, blood pressure, blood lipid, and blood sugar, such that diabetes and cardiovascular diseases caused by metabolic syndrome can be prevented from occurring and developing. BSHE contains high active substance of anthocyanidins, which can provide antioxidant effects, reducing free radicals and diminishing inflammation. BSHE thus can be used for, e.g., weight loss, blood lipid reduction, and prevention of cardiovascular diseases.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A black soybean hull extract (BSHE) comprising components having a molecular weight less than 10000 Da, wherein the BSHE contains 10-45% cyanidin, 10-25% catechin, and 40-80% oligomer proanthocyanidin (OPC), and the total content of polyphenol is over 60%, wherein the BSHE is obtained by:
   (1) extracting crushed black soybean hull with an aqueous solution containing 0.05-0.2% of cellulase or pectinase as a solvent and filtering the extracted solution to obtain a filtration solution;
   (2) filtering the filtration solution with an ultrafiltration membrane to obtain an ultrafiltration filtrate, wherein the molecular weight cut-off of the ultrafiltration membrane is 8000-10000 Da;
   (3) absorbing the ultrafiltration filtrate with an absorbing resin or ion exchange resin and eluting the same with 40-95% ethanol to obtain a purified extract solution;
   (4) condensing the purified extract solution under vacuum to obtain a condensed solution; and
   (5) spray-drying the condensed solution to obtain the BSHE.

2. A composition comprising a BSHE comprising components having a molecular weight less than 10000 Da, wherein said BSHE contains: 10-45% cyanidin, 10-25% catechin, and 40-80% OPC, and the total content of polyphenol is over 60%, wherein the BSHE is obtained by:
   (1) extracting crushed black soybean hull with an aqueous solution containing 0.05-0.2% of cellulase or pectinase as a solvent and filtering the extracted solution to obtain a filtration solution;
   (2) filtering the filtration solution with an ultrafiltration membrane to obtain an ultrafiltration filtrate, wherein the molecular weight cut-off of the ultrafiltration membrane is 8000-10000 Da;
   (3) absorbing the ultrafiltration filtrate with an absorbing resin or ion exchange resin and eluting the same with 40-95% ethanol to obtain a purified extract solution;
   (4) condensing the purified extract solution under vacuum to obtain a condensed solution; and
   (5) spray-drying the condensed solution to obtain the BSHE.

3. The composition according to claim 2, wherein the composition is a dietary supplement or is contained within a foodstuff.

4. A method for improving eyesight in a subject in need thereof, said method comprising administering to said subject an effective amount of the BSHE of claim 1.

5. A method for treating metabolic syndrome, comprising administering to a subject diagnosed with metabolic syndrome an effective amount of the BSHE of claim 1.

* * * * *